United States Patent [19]
Pascaloff

[11] Patent Number: 5,265,343
[45] Date of Patent: Nov. 30, 1993

[54] BLADE COLLET

[75] Inventor: John H. Pascaloff, Goleta, Calif.

[73] Assignee: Hall Surgical, Division of Zimmer, Inc., Warsaw, Ind.

[21] Appl. No.: 826,341

[22] Filed: Jan. 27, 1992

[51] Int. Cl.⁵ .......................... B26B 1/00; B26B 9/00; B25G 3/24
[52] U.S. Cl. ....................................... 30/339; 30/348; 403/322
[58] Field of Search ................. 30/337, 338, 340, 339, 30/348; 403/321, 322, 324, 325, 331; 29/213.1

[56] References Cited

U.S. PATENT DOCUMENTS

| | | | |
|---|---|---|---|
| 2,431,118 | 11/1947 | Heigle | 30/339 |
| 3,805,661 | 4/1974 | Tuomaala | 30/339 |
| 3,943,934 | 3/1976 | Bent | 128/317 |
| 4,386,609 | 6/1983 | Mongeon | 30/348 |
| 4,900,182 | 2/1990 | Stillwagon | 403/322 |
| 4,943,181 | 7/1990 | Murphy | 403/322 |
| 4,960,344 | 10/1990 | Geisthoff et al. | 403/322 |
| 5,135,330 | 8/1992 | Chen | 403/323 |

FOREIGN PATENT DOCUMENTS 2361189 3/1978 France .
579220 7/1946 United Kingdom .

OTHER PUBLICATIONS

Dyonics, Inc. brochure—Cordless Sagittal Saw—Apr. 1, 1986.
Stryker Surgical—Powered Instrumentation for Large Bone Surgery—Date unknown.
Assembly drawing of a drilling device produced and sold by Hall Surgical, Division of Zimmer.

Primary Examiner—Richard K. Seidel
Assistant Examiner—Paul M. Heyrana, Sr.
Attorney, Agent, or Firm—Cary R. Reeves

[57] ABSTRACT

A collet for attaching a blade to a surgical saw is biased toward a closed position in which the blade is securely clamped between a drive member and a clamping member. A rotational movement of a knob is converted into a translational movement of the clamp to open the collet. A mechanism is provided for maintaining the collet in the open position for simplified operation and cleaning.

4 Claims, 2 Drawing Sheets

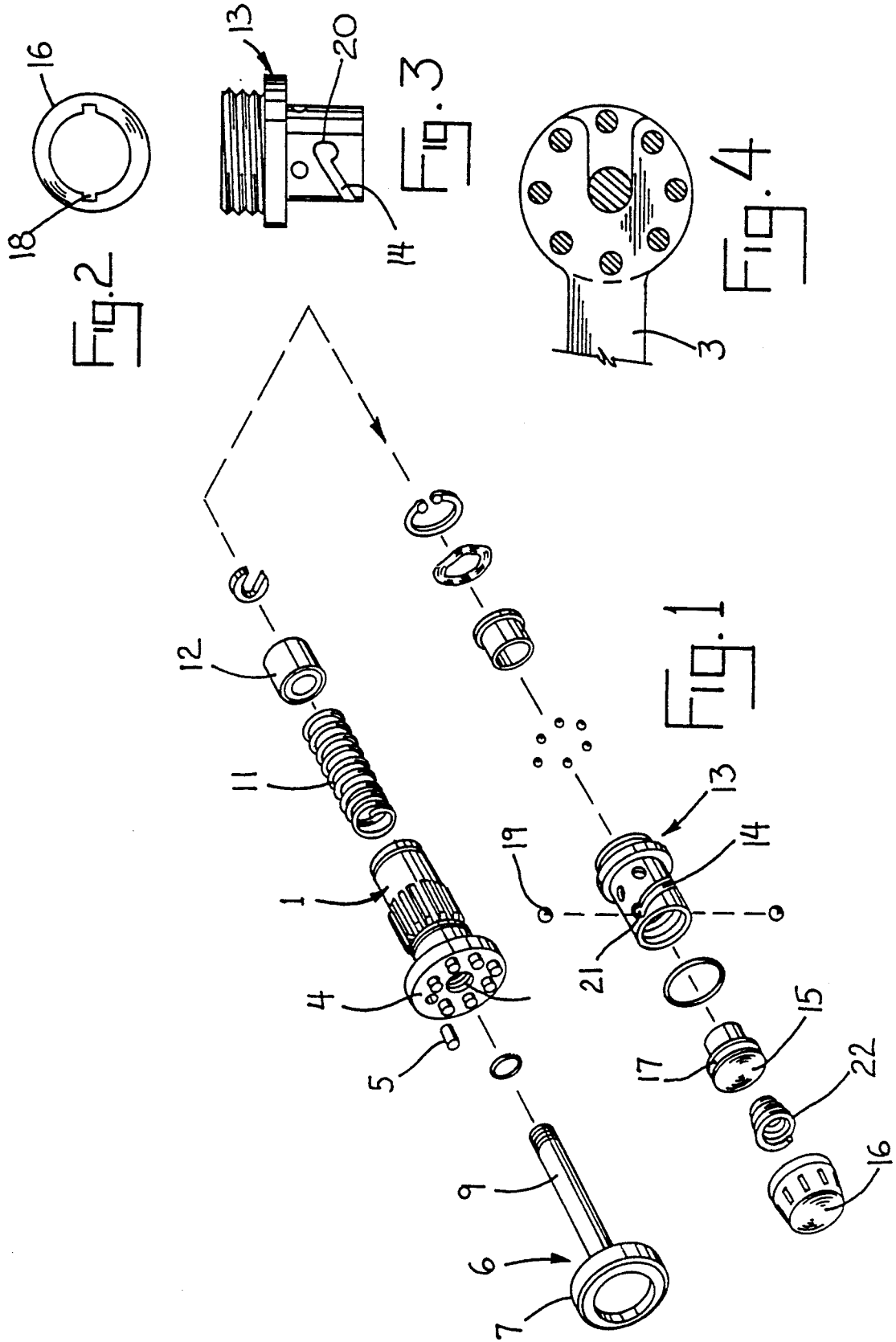

BLADE COLLET

BACKGROUND OF THE INVENTION

The present invention relates to blade attachment mechanisms for surgical saws.

Typical blade collets utilize a threaded stud extending from a drive mechanism and a nut engaging the stud to clamp the blade to the drive mechanism. These collets generally require the use of a separate wrench to turn the clamping nut. Other collets eliminate the need for a wrench by utilizing a nut, such as a wing nut that can be secured without tools. Yet another collet design utilizes a spring actuated clamping plate with extending locking pins for positive engagement with holes in the blade. The blade clamp is moved by finger pressure directed to compress the spring to an open position for receiving a blade. Such collets are limited in that the spring force must be low enough to allow the spring to be readily compressed using direct finger pressure, and low spring force results in a weak grip on the blade. They are also difficult to operate and clean due to the need for the spring to be manually held in a compressed position while a blade is inserted or removed or when the collet is cleaned.

SUMMARY OF THE INVENTION

It is therefore an object of the present invention to provide a blade collet that securely holds and transmits power from a saw to a blade. It is also an object of this invention to provide a blade collet that does not require a separate tool for its operation. It is another object of this invention to provide a blade collet that is easily operated and cleaned. These objects and others are achieved in a collet having a blade shaft for transmitting power to a blade and a blade clamp for holding the blade firmly against the blade shaft. The blade clamp is connected to a knob such that rotational movement of the knob is converted into translational movement to separate the blade shaft and the blade clamp. The blade clamp may be locked in an open position where it is separated from the blade shaft.

BRIEF DESCRIPTION OF THE DRAWINGS

The before mentioned features and advantages of the present invention are apparent from the following detailed description and the drawings wherein:

FIG. 1 is an exploded perspective view of the preferred embodiment of the invention.

FIG. 2 is a plan view of a component part of the preferred embodiment of the invention.

FIG. 3 is a side view of another component part of the preferred embodiment of the invention.

FIG. 4 is a section view taken along line 4—4 of FIG. 6.

DETAILED DESCRIPTION OF THE INVENTION

Figure 6:
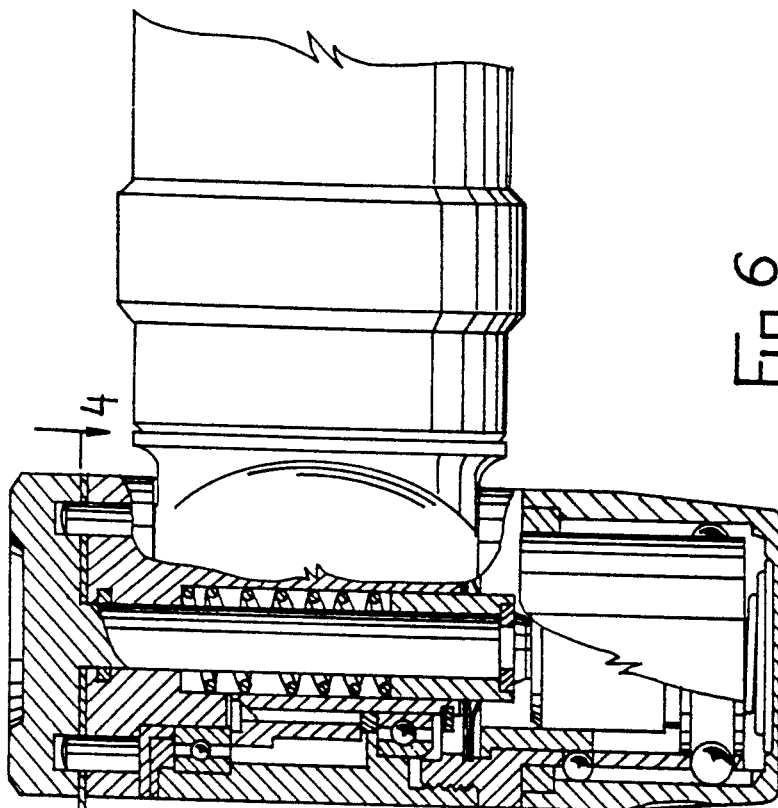
FIG. 6 is a section view similar to FIG. 4 but with the invention in another position of its operation.
Figure 5:
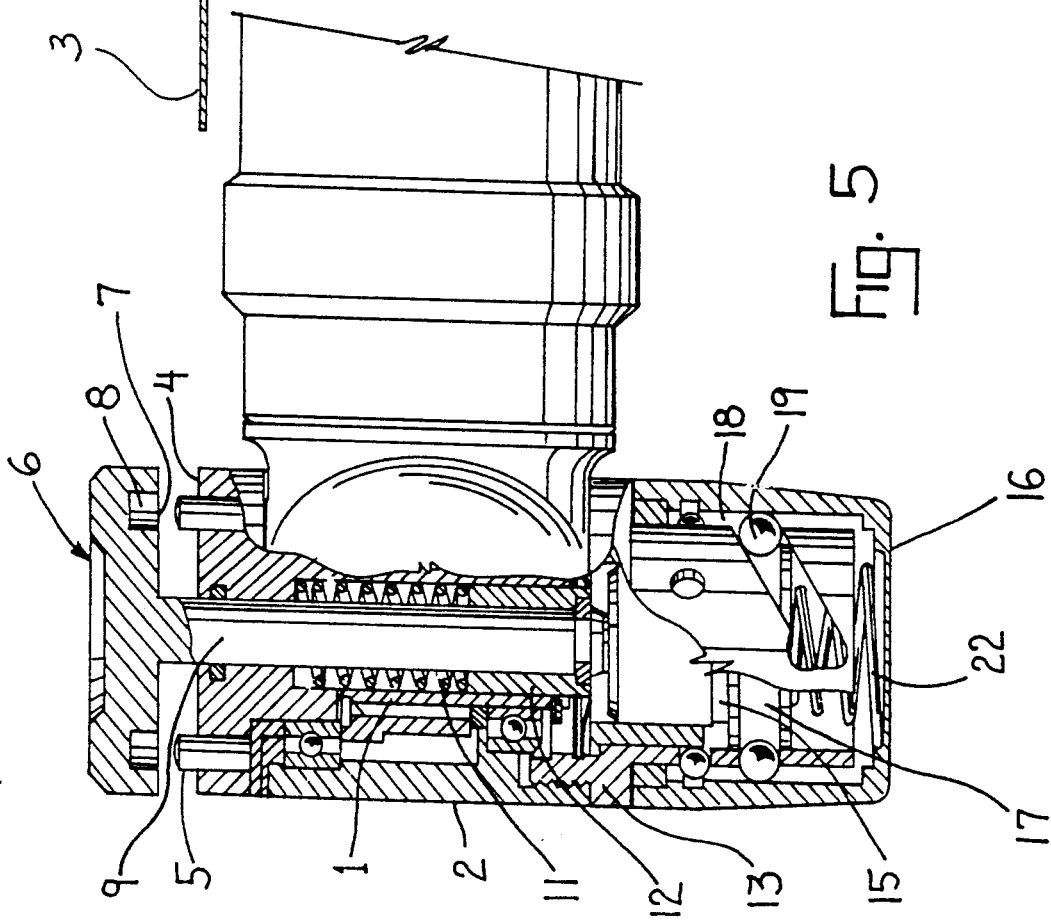
FIG. 5 is a section view of the assembled embodiment of FIG. 1.

Referring to the drawings, FIGS. 1-6 depict a preferred embodiment of a collet for attaching a blade 3 to a surgical saw. A blade shaft 1, or first member, is mounted in a housing 2 in alignment with a first axis. The blade shaft 1 transmits power from a source of power located in the saw to the blade along a second axis perpendicular to the first axis. The blade shaft includes a first clamping surface 4, perpendicular to the first axis, which has upstanding drive pins 5 for engaging the blade. The blade is held against the first clamping surface 4 and in engagement with the pins by a blade clamp 6, or second member, which includes a second clamping surface 7, perpendicular to the first axis, with openings 8 in alignment with the pins. The blade clamp 6 further includes a blade clamp shaft 9 that is slidably mounted in a bore 10 through the blade shaft 1 so that the second clamping surface can translate axially away from the first clamping surface into an open, first, position in which the blade can be inserted for engagement with the blade shaft as shown in FIG. 5. The second clamping surface can move axially toward the first clamping surface into a closed, second, position in which the blade is secure. clamped as shown in FIG. 6. A biasing means, such as a main spring 11, biases the blade clamp toward the closed position. The main spring is disposed around the blade clamp shaft and is constrained at one end by the blade shaft and at another end by a spring retainer 12 connected to the blade clamp shaft.

The collet is opened via a mechanism that translates rotational input into the translational movement of the second clamping surface. This mechanism includes a hollow, cylindrical, grooved retainer 13 fixed to the housing 2. The grooved retainer has a helical groove 14 forming an opening along its wall. Cooperating with the grooved retainer are a plunger 15 and a knob 16. The plunger is disposed for axial movement within the grooved retainer and contains an annular groove 17 about its periphery. The plunger contacts the blade clamp. The knob forms a hollow cylinder open on one end and contains at least one vertical groove 18 formed in its inner wall parallel to the axis as shown in FIG. 2. A ball 19 is disposed in the vertical groove such that, with the plunger disposed in the grooved retainer and the knob rotatably attached to the housing so that its inner wall surrounds the grooved cylinder, the ball 19 protrudes from the vertical groove through the helical groove and into the annular groove as best shown in FIG. 5. Thus, rotational movement of the knob propels the ball, which is confined to move within the vertical groove, along the helical groove. The ball is also confined to move within the annular groove so that as the ball progresses around the helical groove the plunger moves along the first axis. The blade clamp is pushed toward the open position by the plunger when the knob is rotated in one direction and the clamp is returned toward the closed position by the main spring when the knob is rotated in the opposite direction. The above described mechanism provides an operator with a mechanical advantage in opening the collet so that relatively high main spring forces may be employed for better blade retention. Preferably, the knob is spatially separated from the clamping surfaces as shown in FIGS. 5 and 6, where the knob and clamping surfaces are shown approximately 180 degrees from one another on opposite sides of the second axis.

The collet is further provided with a means for locking the blade clamp in the open position for simplified operation and cleaning and the plunger can be locked in the closed position to reduce vibration. This locking action is provided by detents 20 and 21 formed in the helical groove at each of its ends. When the blade clamp is moved into the open position (FIG. 5), the ball may be disposed in a first detent 20 shown in FIG. 3 where it is stably held due to force exerted by the main spring 11. This first detent is such that, when the ball is so disposed, the collet will remain open without operator intervention. In order to return the collet to the closed position the operator need only apply a rotational force to the knob to move the ball from the first detent. When the blade clamp is in the closed position, the ball may be positioned in a second detent 20, shown in FIG. 1, where it is stably held due to force exerted by a conical spring 22 located so as to bias the plunger toward the open position. This reduces vibration in the plunger and knob. The conical spring exerts substantially less force than the main spring so as not to reduce the clamping load exerted on the blade.

It will be understood by those skilled in the art that variations in design and construction of the preferred embodiment described above are possible without departing from the spirit and scope of the invention defined by the appended claims.

I claim:

1. A collet for attaching a blade to a surgical instrument having a source of power, the collet comprising;
   a housing having a first axis and a second axis perpendicular to the first axis;
   a blade shaft mounted in the housing, parallel to the first axis, for transmitting power, along the second axis, from said source of power to said blade, the blade shaft including a first clamping surface perpendicular to the first axis;
   a blade clamp mounted in the housing for movement parallel to the first axis, the blade clamp including a second clamping surface perpendicular to the first axis, the blade clamp being movable between a closed position wherein the second clamping surface is adjacent the first clamping surface and an open position in which the second clamping surface is spaced from the first clamping surface; and
   input means responsive to a rotational input for moving the blade clamp between the open and closed positions, the input means and the first clamping surface being spatially separated from one another and located approximately 180 degrees from one another on opposite sides of the second axis.

2. The collet of claim 1 wherein the means for moving the blade clamp comprises a grooved retainer having a helical groove and a ball linking the blade clamp to the helical groove such that as the ball moves along the helical groove the blade clamp moves between the open and closed positions.

3. The collet of claim 2 wherein the grooved retainer has a detent formed at an end of the helical groove, the ball being positionable in the detent to maintain the blade clamp in the open position.

4. A collet for attaching a blade to a surgical instrument having
   a source of power, the collet comprising;
   a housing having an axis;
   a hollow blade shaft mounted in the housing for transmitting power from said source of power to said blade, the blade shaft including a first clamping surface perpendicular to the axis for contacting said blade;
   a drive pin connected to and extending from the first clamping surface parallel to the axis, the pin being engageable with said blade;
   a blade clamp including a blade clamp shaft disposed for axial movement within the hollow blade shaft between a first position and a second position and a second clamping surface perpendicular to the axis, the second clamping surface having an opening aligned with the pin to receive the pin when the blade shaft is in the second position;
   a main spring disposed around the blade clamp shaft for biasing the second clamping surface toward the first clamping surface;
   a grooved retainer fixedly attached to the housing, the grooved retainer defining a hollow cylinder parallel with the axis and with a wall, the grooved retainer having a helical groove forming an opening along the wall with a first detent at an end of the groove and a second detent at another end of the groove;
   a plunger disposed for axial movement within the grooved retainer, the plunger being adjacent an end of the blade clamp opposite the second clamping surface, the plunger having an annular groove;
   a hollow knob rotatably attached to the grooved retainer, the knob defining an inner wall adjacent the helical groove, the knob having a vertical groove formed in the inner wall parallel to the axis;
   a conical spring disposed within the knob for biasing the plunger away from the knob; and
   a ball disposed within the vertical groove, the ball protruding from the vertical groove into the helical groove and also into the annular groove such that rotational movement of the knob propels the ball along the helical groove thus causing the plunger and likewise the blade clamp to move along the axis, the ball being positionable in the first detent wherein it is stably held due to force exerted by the main spring and the ball being positionable in the second detent wherein it is stably held due to force exerted by the conical spring.

* * * * *